United States Patent [19]
Assini et al.

[11] Patent Number: 5,554,197
[45] Date of Patent: Sep. 10, 1996

[54] HAIR DYING SYSTEM AND METHODS FOR ACCURATELY BLENDING AND DEVELOPING HAIR DYE

[75] Inventors: Anthony Assini, Martinsville; Bernard Foss, Rockaway, both of N.J.

[73] Assignee: Anthony Bernard Incorporated, Martinsville, N.J.

[21] Appl. No.: 277,332

[22] Filed: Jul. 19, 1994

[51] Int. Cl.$^6$ .................. A61K 7/13; A45D 19/00; A45D 40/24

[52] U.S. Cl. .................. 8/406; 8/405; 132/208; 132/209; 132/314; 221/1; 221/95; 221/133; 221/191; 221/206; 222/145.5

[58] Field of Search .................. 8/405, 406; 132/207, 132/208, 209, 314; 221/95, 133, 191, 206, 112, 124, 1; 222/145, 135, 335

[56] References Cited

U.S. PATENT DOCUMENTS

| | | | |
|---|---|---|---|
| 3,581,940 | 6/1971 | Cella | 222/94 |
| 3,651,931 | 3/1972 | Hsiung | 222/136 |
| 3,747,804 | 7/1973 | Raaf et al. | 221/1 |
| 3,809,289 | 5/1974 | Komendowski | 222/83 |
| 3,876,111 | 4/1975 | Swain | 222/94 |
| 3,964,643 | 6/1976 | Morane et al. | 222/145 |
| 3,976,223 | 8/1976 | Jass et al. | 222/94 |
| 4,130,501 | 12/1978 | Lutz et al. | 252/186 |
| 4,184,843 | 1/1980 | Baumann | 8/10.1 |
| 4,358,286 | 11/1982 | Grollier et al. | 8/405 |
| 4,402,698 | 9/1983 | Kalopissis et al. | 8/405 |
| 4,685,931 | 8/1987 | Schieferstein et al. | 8/406 |
| 4,687,663 | 8/1987 | Schaeffer | 424/52 |
| 4,823,985 | 4/1989 | Grollier et al. | 222/1 |
| 4,842,612 | 6/1989 | Rose et al. | 8/406 |
| 4,844,711 | 7/1989 | Hoppe et al. | 8/406 |
| 4,993,594 | 2/1991 | Becker et al. | 222/136 |
| 5,021,066 | 6/1991 | Aeby et al. | 8/405 |
| 5,078,748 | 1/1992 | Akram et al. | 8/405 |
| 5,088,627 | 2/1992 | Musel | 222/145 |
| 5,100,436 | 3/1992 | Wenke | 8/406 |
| 5,100,658 | 3/1992 | Bolich, Jr. et al. | 8/405 |
| 5,102,655 | 4/1992 | Yoshihara et al. | 8/405 |
| 5,131,912 | 7/1992 | Ehara et al. | 8/406 |
| 5,207,798 | 5/1993 | Cotteret et al. | 8/406 |
| 5,221,286 | 6/1993 | Singleton et al. | 8/406 |
| 5,387,034 | 2/1995 | Bauer et al. | 222/145 |

OTHER PUBLICATIONS

Material Safety Data Sheet, Carbopol Resins, Carbopol High Performance Polymers, pp. 1–6, Jan. 1989.
BASF, Pluronic Polyols in Cosmetics, pp. 1–17. 1972.

*Primary Examiner*—Paul Lieberman
*Assistant Examiner*—Caroline L. Dusheck
*Attorney, Agent, or Firm*—Lerner, David, Littenberg, Krumholz & Mentlik

[57] ABSTRACT

The present invention relates to methods and systems for hair dying. The system includes at least two reservoirs containing different hair dying components in predetermined concentrations, the containers including outlets having cross-sectional areas which are sized relative to the concentration of the component contained in the reservoir and the amount of that component needed to react with the remaining components. The measuring device calibrated with respect to the concentrations of the hair dye components and the cross-sectional areas of their respective reservoir outlets, permits rapid and accurate dispensing of the hair dye components in the proper quantities. In a preferred arrangement, the measuring device is provided on a blending board so that the components can be blended together immediately upon dispensing.

17 Claims, 3 Drawing Sheets

HAIR DYING SYSTEM AND METHODS FOR ACCURATELY BLENDING AND DEVELOPING HAIR DYE

FIELD OF THE INVENTION

The present invention relates to the field of hair care and, in particular, hair dying.

BACKGROUND OF THE INVENTION

Hair dying is often a difficult, messy and complex procedure even for hair care professionals. Such professionals need to be skilled in applying hair dying compositions and must be able to consistently and repeatedly blend a diverse number of coloring, coupling and developing agents to provide a client with a desired hair color.

Hair dyes and other additives used in hair dye formulations exist in any number of different delivery or carrier formats. For example, dyes may be powdered or granulated, may be in the form of a free flowing liquid, or may have a gel, cream or paste format. Each different format requires different measuring, mixing and handling equipment. These different formats exemplify one of the problems faced by hair professionals who seek clean, simple, rapid and repeatable means for effecting hair dying.

Another impediment faced by hair care professionals in finding such a clean, simple and repeatable hair coloring process is the fact that oftentimes a plurality of dyes must be mixed to achieve the desired color. In and of itself this presents a major headache for hair care professionals which is made even worse by the fact that the components of the hair dye may be in different delivery formats.

The solubility or mixability of a first dye or bleach in, for example, powder form may be poor when the second dye used is in the form of a viscous cream or paste. Often homogeneity is also a problem. If the first dye is not completely dissolved or completely and homogeneously dispersed within the second dye, or visa versa, then upon activation, "pockets" of color may develop. If these "pockets" of color were applied to a client's hair, the resultant hair color would be most unsatisfactory, leaving the client with leopard-like spots of hair coloring. Moreover, it is possible that, if poorly mixed, one dye could be activated to a considerably greater degree than the second dye. As the useful life of a dye once activated is relatively short, disparate activation times can also lead to anomalous results. To further complicate matters, various dyes and developers are frequently provided in different concentrations, greatly complicating the formulation of custom colors, making such tasks onerous.

Most of the dyes utilized in accordance with the present invention, and within the industry, are oxidative dyes which require an oxidative developer such as peroxide. However, the peroxide developer can be provided in many of the same delivery formats as the hair dyes. Thus, the solubility and/or mixability of an additional necessary component must be considered.

To put these matters in a real life context, an exemplification of a "real life" scenario is set forth. Consider a custom color which requires three dyes (A), (B) and (C). Hair dye (A) is provided in the form of a powder. According to the directions provided by the dye manufacturer, 100 grams of hair dye (A) will dye approximately ½ of a head of medium thickness shoulder length hair. Hair dye (B) is provided in a liquid form. According to the manufacturer's recommendation, hair dye (B) is formulated such that 50 ml will completely dye approximately the same amount of hair as 100 grams of hair dye (A). Unfortunately, hair dye (B), while in liquid form, has a very high surface tension. As such it would be difficult to wet and dissolve hair dye (A) in hair dye (B).

Hair dye (C) is provided in a form of a paste. Fifty grams of hair dye (C) will completely dye approximately ⅓ of a head of medium thickness shoulder length hair. Hair dye (C) is neither soluble in the liquid hair dye (B) nor easily mixed with hair dye (A).

Obviously, preparing a custom color from these three dyes would be difficult. None of the three dyes are easily soluble or blendable with the others so as to allow for the formation of a homogeneous mixture. This can dramatically affect the nature and quality of the resulting hair dye color. Second, each of the dyes requires different measuring and metering tools. Third, because the scales provided by the various manufacturers for the amounts of dye needed to color a certain amount of hair are different, the hair care professional will have to manually adjust the amount of hair dyes (A), (B) and (C) so that uniform hair dying capacity is maintained.

A more complex problem develops if the custom color formulation contemplated requires, for example, twice as much hair dye (A) as hair dye (B) or (C). Hair dye (A), being a powder, may not be blendable or dissolvable in lesser amounts of a liquid and paste. A hair care professional will thus face significant scaling problems particularly in attempting to ensure the correct amount of hair dye (C) is utilized. The difficulties in blending the disparate components show themselves in other ways as well. For example, the activity of the components of a hair dye may start to diminish before the second hair dye, with which the first hair dye is to be mixed, is fully activated. If hair dyes (A) and (B) were mixed in the absence of appropriate activation levels, the uniformity of the hair coloring mixture would be affected. Finally, if a hair care professional intended to use the aforementioned formulation as only one of a number of colors, i.e. as in streaking, then the entire dye formulation may have to be scaled down, complicating the formulation and dying process even further.

Although the difficulties of proper hair coloring which face a hair care professional are certainly clear, the problems become even more stark when the environment in which a hair care professional operates is considered. Hair care professionals work in beauty shops or salons. They do not work in chemistry labs; they do not have the benefit of accurate metering equipment; and the mixing and formulation of appropriate hair color must be done in the hub bub of a salon—people talking, phones ringing, hair being cut; in other words amidst great commotion. On top of all this, the stark economic constraints of operating a retail hair salon or beauty shop come into play as hair care professionals have only a limited amount of time to work on developing hair color before the time expended becomes economically excessive.

Cognizant of the aforementioned myriad of problems faced by hair care professionals, the inventors have addressed these needs, in particular, the problems of accurate and repeatable dye formulation. The present invention provides a solution which is simple yet profound, enabling even the unskilled to repeatedly prepare correct dye formulations, without mess, health risk, or inconvenience. Moreover, the resulting dye compositions are convenient to use and apply because they can be prepared in a series of smaller batches and applied by a brush.

SUMMARY OF THE INVENTION

It is an object of the present invention to provide a hair dying system and a method of blending and formulating hair dye which is convenient, repeatable and consistent. Therefore, in accordance with the present invention, there is provided a hair dying system including a developable hair dye contained within a first hair dye reservoir; a developer capable of developing the hair dye, the developer being contained within a first developer reservoir; and a means for dispensing the hair dye from the first hair dye reservoir and the developer from the first developer reservoir. The system further includes a means for blending the hair dye and the developer, the blending means including at least one measuring means for measuring an amount of the developer and/or the hair dye when dispensed.

The hair dying system of the present invention can also include a plurality of dispensing containers each having at least one dispensing orifice of a preselected cross-sectional area, each such container including at least one dispensable component of a hair dying system. At least one of the aforementioned dispensing containers includes a developable hair dye, said hair dye having a preselected concentration. Another of the dispensing containers includes a developer capable of developing said hair dye, with the developer also having a preselected concentration which may be the same or different when compared to the concentration of the hair dye.

A measuring means for measuring the amount of the hair dye and the developer dispensed from each such container is provided. The measuring means includes a scale. The scale and the cross-sectional areas of the orifices of the dispensing containers are preselected and calibrated, based in part upon the preselected concentrations of the hair dye and the developer, such that the amount of dispensed developer correlates to the total amount of hair dye dispensed as measured by the measuring means. A blending means for blending the dispensed hair dye components is also provided.

Another aspect of the present invention provides a method of blending a developable hair dye and a developer which includes a plurality of steps. The first step includes providing a means for blending a first hair dye and a developer capable of developing the first hair dye. The means for blending should include at least one measuring means. The measuring means is preferably geometric indicia such as lines, marks or shapes sized and shaped to permit easy measuring and proportioning of the hair dye or the developer when dispensed. The next step involves dispensing a first amount of the first hair dye as measured by the length or volume of the geometric indicia. Next, a first amount of the developer sufficient to develop the first amount of the hair dye is dispensed. Finally, one intimately intermixes the first hair dye and the developer such that the hair dye is developed.

The present invention provides a dye blending system which allows for a great deal of flexibility and ease of use. The system and methods of its use can best be explained by reference to a relatively simple example in which a first container is provided containing an oxidative hair dye, in gel form, having a concentration of 10.0 mg of dye per gram of gel. The first container containing the oxidative hair dye includes means for dispensing the oxidative hair dye which is designed to include a dispensing orifice sized and shaped to deliver a column of gelled dye such that approximately 100 grams of gel will be dispensed in a linear inch. At this dye concentration and linear volume, about 1.0 gram of dye would be dispensed per inch. In the present exemplification, one inch of hair dye containing gel will, when developed, dye approximately one tenth of a head of women's shoulder length hair of medium thickness and consistency.

A second dispensing container is also provided containing a hydrogen peroxide based developer. Preferably, the developer is also in the form of a gel and has a concentration which is the same as that of the hair dye. Also, preferably, the inside diameter or cross-sectional area of the dispensing orifice of the second dispensing container is made substantially identical to that of the orifice provided for the oxidative hair dye. Therefore, an equal amount of developer, as measured on a linear basis compared to the length of the dispensed column of hair dye, will be delivered per inch dispensed.

Also in accordance with the present invention, the hair dying system includes a means for blending the hair dye and the developer. In a relatively simple embodiment, this means for blending may be a flat piece of glass, or other non-absorbant, inert, flat-surfaced material. Disposed thereon or therein are measuring means for measuring the amount of hair dye and developer dispensed. For simplicity, the measuring means may be two straight lines each one foot long having graduations at one inch intervals.

To blend the correct amount of hair dye and developer for the entire head of hair (using the exemplary standard 1 inch=$\frac{1}{10}$ head of shoulder length hair of medium thickness and consistency), a hair care professional need only dispense a consistent column of hair dye ten inches long. This can be easily accomplished by placing the dispensing end of the first dispensing container containing the developable hair dye adjacent one end of one of the geometric indicia and dispensing hair dye until the ten inch graduation is reached. Because, in this case, the developer is packaged and compounded in a manner substantially identical to the hair dye, the hair care professional need only dispense a ten inch column of developer adjacent to or on top of the second graduated line. Thereafter, using a spatula or other such device, the hair dye and the developer are intimately intermixed such that the developer can react with the oxidative hair dye and activate or develop same. Of course, it is also possible to merely apply the hair dye in a linear column on one side of a single graduated line and the developer on the other side of the same graduated line.

Preferably, both the hair dye and the developer are provided in the form of a gel, cream or paste having sufficient viscosity to resist significant spreading upon dispensing. For example, both the developer and the hair dye can have the consistency of various toothpastes or toothgels which, when dispensed, maintain a substantially columnar shape for a reasonable period of time, i.e. at least about ten to thirty seconds. This allows great control and ease of both blending and use. Of course, some flattening is to be expected, particularly where the column contacts the blending means.

While the foregoing discussion underscores the simplicity of the use of the present invention under relatively uncomplicated conditions, it does not properly emphasize the ease and flexibility of the system under more demanding applications. This can be shown when, for example, a hair care professional desires to mix two or more different color dyes into a single formulation to create a customized color.

In accordance with the present invention, all of the hair dyes can be formulated and packaged such that each has an equal concentration and substantially uniform dispensed form. Therefore, instead of, for example, having to measure out 6 fluid ounces of a first dye, 5 grams of a paste and 2 ounces of a powder to derive a specific color, the formula could be reformulated in terms of, for example, some number of inches of a first dye, some number of inches of a second dye, and some number inches of a third dye. The same number of inches of developer could be dispensed and measured as previously described. All of the materials could then be blended together by intimately intermixing the developer and dyes.

As will be readily appreciated, it will also be easier to measure out fractions of an inch to scale-up or scale-down the formulations of the present invention as opposed to having to weigh and/or volumetrically measure out components as required in the prior art.

The present invention also provides for flexibility in terms of accommodating the chemistry of the various hair dyes and developers used. For example, while a first dye may be provided at a concentration of up to 10 mg per gram of gel, a second hair dye may have a lower maximum concentration. If, for example, the second hair dye is only available at concentrations of 5 mg per gram, one merely needs to meter and measure 2 inches of the second hair dye to provide the same hair dying potential as 1 inch of the first hair dye. Alternatively, the dispensing orifice of the dispensing container for the second dye can be modified to have twice the cross-sectional area when compared to the dispensing orifice provided in connection with the first gelled dye. A linear inch of the second dye will then have the expected quantity of dye. Of course, the one inch column will be substantially thicker than the first column of dye.

Separate geometric indicia or other measuring means could also be provided for each of the hair dyes of differing concentrations. In this way, one unit of each dye would be metered and dispensed relative to the scale appropriate for a dye of that concentration. Each unit of dye would provide the same amount of dye or the same dying capacity. However, each unit of each different dye would have a different concentration and a different volume.

Finally, the second dye having a concentration of 5 mg/1 gram of gel could be used as the basis for the entire dying system. This would be particularly useful if the second dye had the lowest possible maximum concentration of all of the dyes used in the hair dying system. All of the other dyes could certainly by formulated at that same concentration.

As will be readily appreciated, because of the flexibility and inherent accuracy of the present invention, skilled hair care professionals need not pay the kind of attention to hair dye formulation as required previously. Less time spent formulating means more customers that can be serviced in a given period of time. Greater consistency and accuracy means satisfied customers coming back time and time again.

DETAILED DESCRIPTION OF THE PREFERRED EMBODIMENT

Figure 1:
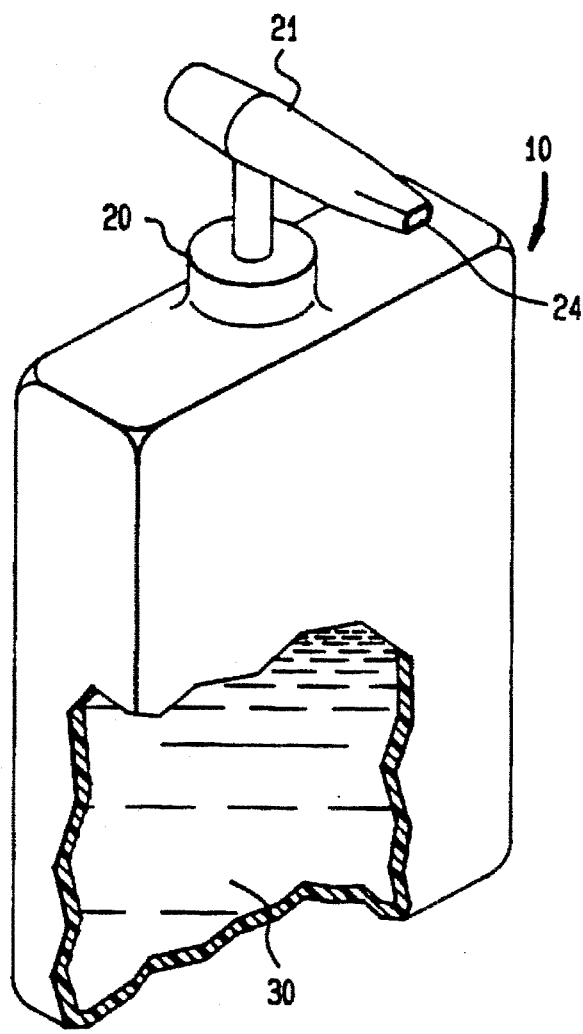
FIG. 1 is a side view, in partial cross-section, of a container including one form of pump dispenser.

Any developable hair dye and developer which are capable of being compounded and delivered in a gel, cream, paste or other format of sufficient viscosity may be used in accordance with the present invention. Preferably, however, oxidative hair dyes and peroxide based developers are used. Various hair dying and developing compositions useful in accordance with the present invention are described in, for example, Aeby et al. U.S. Pat. No. 5,021,066; Singleton et al., U.S. Pat. No. 5,221,286; Cotteret et al. U.S. Pat. No. 5,207,798; Hoppe et al. U.S. Pat. No. 4,844,711; Haddad et al. U.S. Pat. No. 4,927,527; and Schieferstein et al. U.S. Pat. No. 4,685,931. The texts of the aforementioned patents are hereby incorporated by reference. The terms "hair dye(s)" or "hair dying composition(s)" as used herein is meant to include hair bleach as well.

The delivery formats or carriers used in accordance with the present invention may be, as previously discussed, gels, creams or pastes. Any other delivery format which meets the criteria set forth herein may also be used. The carrier must be capable of providing hair dye and developer which are sufficiently viscous so as to avoid substantial spreading upon being dispensed. The phrase "substantial spreading upon being dispensed" should be understood to mean that the hair dye and developer containing formulations can be dispensed from a container as a ribbon, column or the like and substantially maintain the dispensed shape. This must be accomplished without significant running or spreading for a predetermined period of time, even if the surface to which the material is applied is inclined. Gels and pastes having viscosities similar to commercial toothpastes and toothgels, for example, make a suitable analogy. Viscosities well below that of toothpastes are also contemplated. The dispensed shape of the material should roughly be maintained for at least about 10 to about 30 seconds. On the other hand, the formulations should not be so viscous as to make blending and application difficult.

More specifically, the hair dye containing component of the hair dying system of the present invention should have a viscosity of between about 500 centipoise ("cps.") and about 3,000,000 cps., more preferably between 10,000 cps. and about 1,000,000 cps, and, most preferably, between about 20,000 cps. and about 500,000 cps.

For the developer, the viscosity generally ranges from between about 20,000 cps. and about 3,000,000 cps. More preferably, the viscosity ranges from about 50,000 cps. to about 1,000,000 cps. Most preferably, the viscosity of the developing component of the hair dying system includes between about 70,000 cps. and about 500,000 cps.

Most preferably, in accordance with the present invention, both the hair dye containing component of the system and the developer containing component of the system are in the form of a gel.

Concentration in accordance with the present invention will depend upon a number of factors. The first criteria is the dye carrying capacity of a particular delivery format relative to a particular dye. For example, a particular dye may be properly dissolved or emulsified within a gel formulation in up to about 30% of the weight of the gel. The same dye may be susceptible to higher concentrations in a paste or cream format. Other dyes using the exact same carrier vehicles may only be susceptible to lower concentrations in all three formats.

However, other than the maximum concentration available for a particular dye in a particular carrier, other factors will generally control concentration. In a preferred embodiment in accordance with the present invention, a system is contemplated whereby a number of colored dyes are provided such that they can be easily and interchangeably used and intermixed. In that eventuality, the highest concentration for each of the dyes used would likely be no higher than the highest possible concentration of the least soluble or emulsifiable dye used as part of the system. At the very least, the concentration of dye ingredients of various formats may be selected in such a way to assure that all of the possible dye and carrier formulations can be compounded to the same concentration without significant stability or separability problems.

In general, however, the concentration of dye within a gel carrier should range from about 0.01% to about 5.0% by weight of material going into the finished gel compared to the weight of the finished gel ("w/w") and more preferably from about 0.01% to about 4.0% w/w. The concentration of dye in a cream will generally range from about 0.01% to about 5.0% w/w and more preferably from about 0.01% to about 4.0% w/w.

In a paste form, the dye should have a concentration between about 0.01% and about 5.0% w/w and, more preferably, between about 0.01% and about 4.0% w/w.

Similarly, the concentration of the developing agent will depend both on the type of developing agent used and the carrier format. In addition, the developer should be formulated to accommodate the needs of the system. In the present invention, the developer should be formulated to provide a concentration which is easily scaleable and which accommodates the concentration of the dyes used. Preferably, all of the dyes and the developer in the system will have an identical concentration. Therefore, one measured unit of dye will be developed by, preferably, one equally measured unit of developer.

Assuming that the developer is a peroxide and, more preferably, hydrogen peroxide, then the concentration of the developer should generally range from about 1.5% to about 33.0% w/w, and preferably between about 3.0% and about 12% w/w if formulated within a gel.

A particularly advantageous gel formulation in accordance with the present invention can be used as a delivery format for both hair dying agents and peroxide developers. The formulation includes a carbomer such as CARBOPOL 940 available from BF Goodrich. CARBOPOL 940 is an acrylic acid homopolymer of carboxypolymethylene having the general formula $(CH_2CHCOOH)_n$. The carbomer should be provided in an amount between about 0.25 and about 5 weight percent based on the total weight of the formulation. More preferably, the carbomer could be present in an amount between 0.25 and about 5%, and most preferably in an amount between 0.75 on about 2% by weight. Other functionally similar polymers may be used in place of CARBOPOL 940.

A polyoxamer such as, for example, PLURONIC F-127 available from BASF Wyandotte Corporation could also be used. PLURONIC F-127 is a 407-polyoxypropylene-polyoxyethylene block copolomer which may be provided in an amount between about 0.5 and about 10% by weight of the formulation and, more preferably, between about 1 and about 3 wt. %. The polyoxamer acts as a surfactant and penetrant. Of course, almost any food, cosmetic or pharmaceutically acceptable surfactant can be used such as, for example, sodium lauryl sulfate, polysorbate 20, and nonoxynol-9.

When using a hydrogen peroxide based formulation as developer, it is important that the polyoxamer used be a non-ionic surfactant. However, if the gel formulation is used in connection with, for example, hair dyes, it may be possible to substitute other conventional ionic surfactant in its place.

Triethanolamine (TEA) could also be provided as a cross-linking agent, although other cross-linking agents are acceptable such as, NaOH, KOH, di-2-ethylhexylamine, ethoxylated coco amine or di-isopranolamine. When triethanolamine is used, the amount should range from about 0.2 to about 1% by weight of the total formulation, and, more preferably, from about 0.3 to about 5 wt. %.

When a hydrogen peroxide based developer is contemplated, up to about 40% of the formulation by weight can be composed of up to about a 50% solution of a 100% hydrogen peroxide. Greater amounts of lower concentration peroxide solutions may also be used.

The balance of the formulation should be water, preferably distilled or deionized water and most preferably, distilled, deionized water. The pH of the resulting formulation, particularly for peroxide developer based gels, should range between about 1 and 9. More preferably, the pH should range from between about 2 and about 7 and most preferably between about 2 and about 5. Most preferably, the resulting gels are clear and have a viscosity which ranges from about 50,000 to about 400,000 cps.

Figure 2:
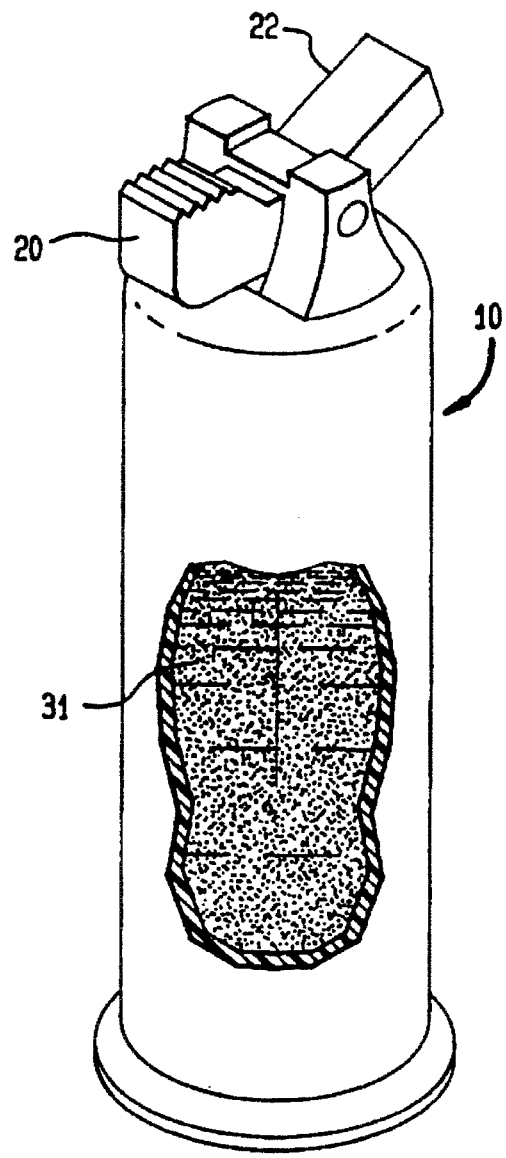
FIG. 2 is a side view, in partial cross-section of a container including a second form of pump dispenser.
Figure 3:
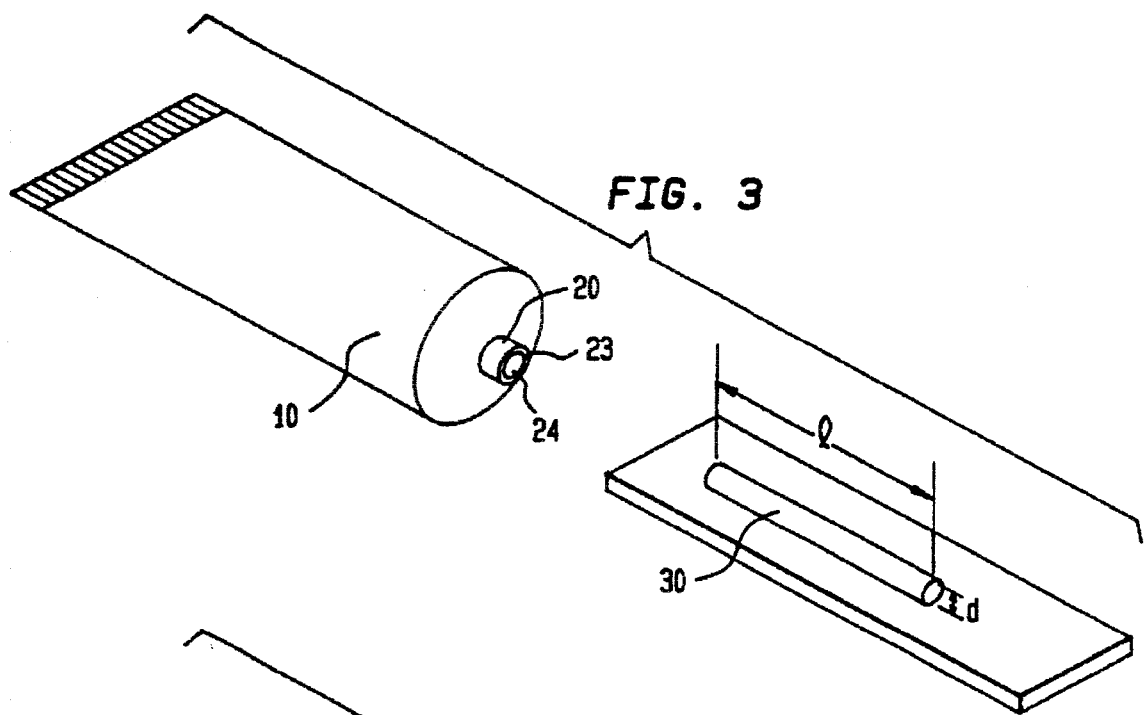
FIG. 3 is a perspective view of a container in accordance with the preset invention having a nozzle for dispensing material with an orifice of a defined cross-sectional area and a circular shape which is substantially the same as the shape and cross-sectional area of the material dispensed through said orifice.

Of course, while the formulation of the dyes and developers used in accordance with the present invention are important, so is the manner in which the formulations are delivered. This aspect of the present invention will be better understood by reference to the figures. As shown in FIGS. 1, 2 and 3, a reservoir or container can be provided for retaining and dispensing dye or developer containing formulations. As these figures show, the container or reservoir can have any desirable shape, size and construction so long as it is substantially non-reactive to the contents contained therein. Where the contents of the container are light-sensitive, the container should be constituted from materials which will block wavelengths of light which might cause reaction or product degradation. It is also possible for a single container to include a plurality of reservoirs for different dyes and developers, and at least one dispensing means. For example, a single container may be provided having two or more reservoirs of the same or different volume. A dye and a proportionately formulated developer can be housed in each of the separate reservoirs, and a single dispensing means may be provided with a plurality of orifices such that both the dye and the developer can be dispensed together. Alternatively, separate dispensing means for each reservoir may be provided.

More specifically as shown in FIG. 1, the container 10 may be formed from semi-rigid, squeezable, opposed walls in a shape traditionally used for dispensing hand creams, lotions, hair care products and the like. Alternatively, as shown in FIG. 2, a rigid or semi-rigid container such as those used in a toothpaste pump dispenser may be used. Frequently, however, and as shown in FIG. 3, container 10 may be in the form of a tube sealed at one end and having a dispensing means disposed in the opposite end. The reservoir or container 10 can have any other shape desired and may be made of any appropriate material, such as glass, paper, plastic, metal foils, composite materials and combinations of the same.

Each container 10 should include a dispensing means 20 which may be, as shown in FIG. 1, a pump 21 such as those used in dispensing liquid soaps; a pump 22, as shown in FIG. 2, such as those used in connection with the dispensing of toothpastes; or a nozzle 23, as illustrated in FIG. 3. Each dispensing means 20 includes a dispensing orifice 24 having a predefined shape and cross-sectional area. A dye formulation useful in accordance with the present invention, due to its viscosity, substantially assumes the shape of the dispensing orifice 24 as it is dispensed. Referring to FIG. 3, dispensing orifice 24 is in the shape of a circle having a defined diameter d. The resulting column of material 30 dispensed through orifice 24 also has a cross-sectional shape which is substantially circular with a diameter of approximately d. The volume of material dispensed is controlled by the equation $V=\pi r^2 l$ where $r=\frac{1}{2}$ of diameter d, $\pi$ is a constant and l is the length of the column. If the concentration of the dye or developer is represented by "N", then the amount of "A" dye or developer dispensed would be controlled by the equation A=NV.

Figure 4:
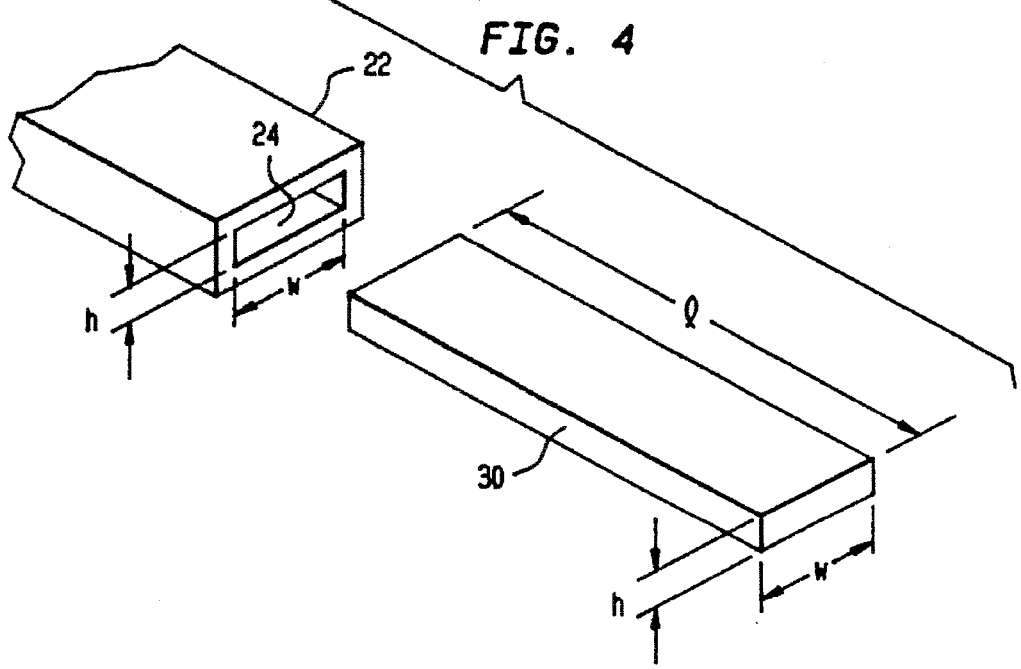
FIG. 4 is a perspective view of a second nozzle for dispensing material with an orifice of a defined cross-sectional area and a rectangular shape which is substantially the same as the shape and cross-sectional area of the material dispensed through said orifice.

Of course, as shown in FIG. 4, the dispensing orifice 24 can have any shape such as, for example, a rectangle. In that case, the orifice will have a height of "h" and a width of "w". The column of material 30 dispensed from a container 10 having a rectangular orifice 24 will also have a cross-sectional shape which is substantially rectangular with approximately the same height and width as the orifice 24. The volume of the dispensed column of material 30 would, under these circumstances, be controlled by the equation V=w×h×l, wherein l is the length of material dispensed. Again, the amount of a component actually dispensed for a given column of material can be determined by multiplying the volume V dispensed by the concentration N of the component as previously described.

In one preferred aspect of the present invention, single use dispensing tubes can be provided. The size and volume of the tube can be precalculated to deliver sufficient material to dye, short, medium or long hair. In an additional embodiment, both the hair dye and developer can be dispensed simultaneously from a single, single use device.

Another important aspect of the present invention and another deficiency of the prior art involves measuring. It is important in accordance with the present invention to provide a convenient, useful, and repeatable way to measure the dispensed components of the hair dying system. Therefore, measuring means 80 is provided. Measuring means 80 may be, for example, a graduation on the side of container or reservoir 10 which allows one to derive the volume of the material dispensed relative to the amount displaced from the container. Alternatively, pumps 21 or 22 can be designed to provide for an accurate metering such that fully depressing the pump or a lever actuating the pump would provide a fixed volume of material. Preferably, however, measuring means 80 is not associated directly with the reservoir or container 10.

Figure 5:
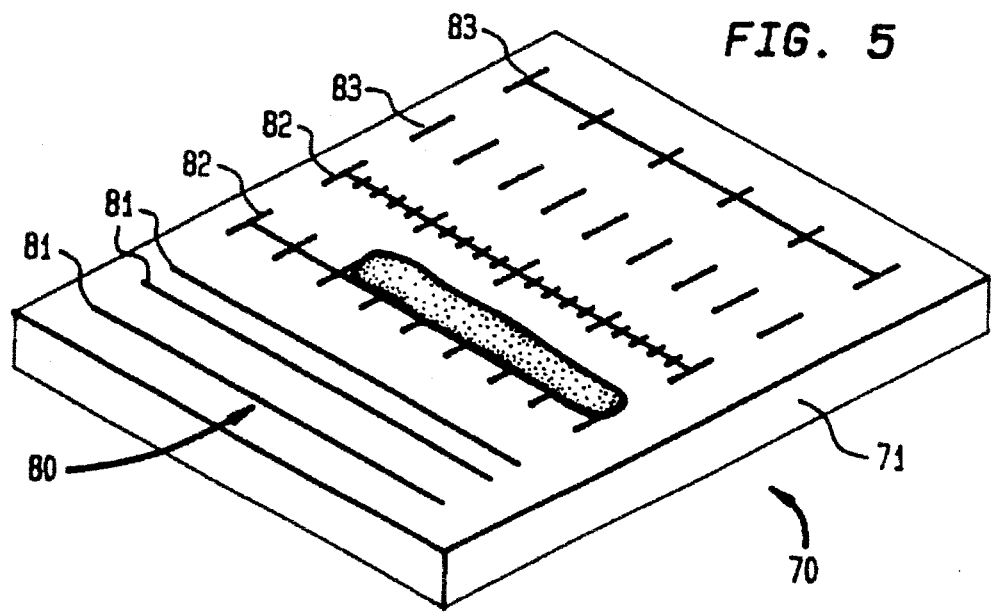
FIG. 5 is a perspective view of a blending means in accordance with the present invention including measuring means and a column of dispersed material dispensed adjacent such measuring means.

As shown in, for example, FIG. 5, measuring means 80 may be disposed on or associated with a blending means 70 for blending dispensed hair dye components including the hair dye, the developer, coupling agents, fixative agents and the like. Blending means 70 may be a flat or substantially flat board 71 formed from a substantially rigid material such as plastic, glass, metal or treated paper or a laminated or multi-layered material. Blending means 70 should allow the hair dying components to be easily measured out, blended and removed without absorption, interaction, or substantial adhesion.

In a particularly preferable embodiment, blending means 70 is a pad 72 with removal pages 73, each of which is made of paper or other disposable material which has been treated such that it will not quickly absorb the hair dying components when placed thereon. After each batch of dye has been compounded, the page 73 just used for blending can be pulled from pad 72 and disposed of as normal garbage. This saves considerable clean-up time. In addition, the pages 73 can have a perforated section (not shown), which would allow the hair care professional to write the customer's name and formulation down. This perforated section could then be detached prior to disposing of the page 73 and placed in a ROLODEX or card file for easy reference.

Figure 6:
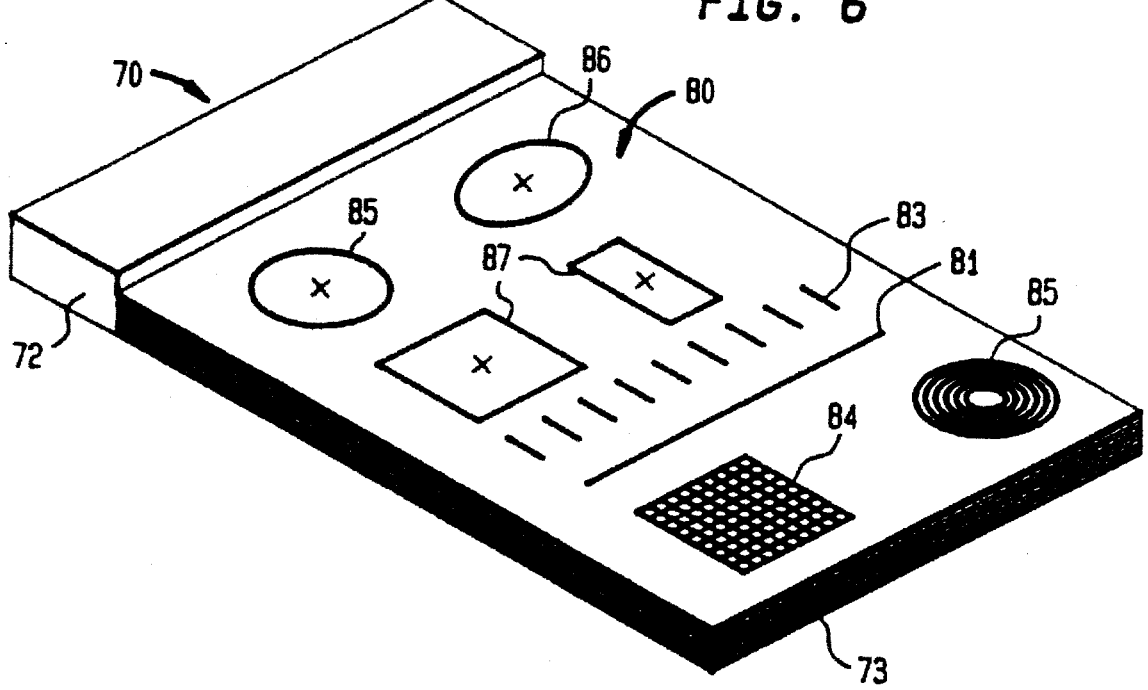
FIG. 6 is a perspective view of a disposable blending means including measuring means.

As shown in FIGS. 5 and 6, the measuring means 80 may be disposed on blending means 70. In a particularly preferred embodiment, the measuring means 80 is a geometric shape or a line. More preferably, measuring means 80 is "geometric indicia" having a geometric shape or being a line which is used as the basis for measuring the amount of dispensed dying components. As used herein, the term "geometric indicia" includes, for example, a line 81, a graduated line 82, a series of parallel lines 83 such as the markings on a conventional thermometer, or a grid 84 like that found on graph paper 84. Geometric indicia may also include circles 85, ovals 86, or polygons 87.

The size and/or dimension of the geometric indicia making up the measuring means 80 is, at least in part, responsible for controlling not only the amount of dye compounded for use, but also the formulation thereof. Therefore, the measuring means 80 must be calibrated to the concentration of the hair dying components and the dying capacity of the dye, as well as to the cross-sectional area of the dispensing orifice 24. In designing the system, the scale or the length of the units of measure defined by, for example, a graduated line 82 used as measuring means 80, need not be controlled by a conventional distance such as, for example, inches, meters, or the like. Rather, the length of a unit of measure may be arrived at as a function of the concentration of the hair dye used and the dying capacity of the dye, as well as the amount of hair dye dispensed in a column.

For illustration purposes, assume that one ounce of hair requires one gram of activated dye to produce the desired color change. Assume also that all of the various dyes used in a particular system have the capability of producing the expected change in color based on the same proportion of dye to hair. The measuring scale provided, the cross-sectional areas of the orifices 24 of the dispensers 20 of the containers 10, and the concentrations of the dyes should be so configured that one unit of dispensed gelled dye includes one gram of activated or activatable hair dye. Consequently, one unit dispensed will contain sufficient material to dye one ounce of hair.

In practice, any one or some combination of these variables may be adjusted. For example, it may be easier to supply hair care professionals with a single blending means 70 including preset measuring means 80. To accommodate that preset scale, adjustments would have to be made to the concentration of the dye or to the size of the dispensing orifice 24 to ensure that each scale unit contains the same relative dying capacity.

If the measuring means 80 is, for example, a straight line 81, a graduated straight line 82 or a series of parallel spaced lines 83, then to obtain a specific amount of dye or developer, one need merely place the dispensing means 20 of, for example, container 10 adjacent one end of the line 81 and 82 (or, the first parallel line 83) and pump or squeeze the container 10 while moving the container 10 along the line until sufficient material, as measured thereby, has been delivered. In the case of, for example, a circle 85, measuring can be accomplished by dispensing sufficient material to cover the entire circumference of the circle or to fill the area contained within the circle 85 as desired. A plurality of different circles 85, or a series of concentric circles 85 can be provided, their dimensions calculated based on circumference or area as desirable, to allow for larger and larger quantities of material to be utilized. The same holds true for use of a polygon 87 such as a square, triangle or the like, or an oval 86. Additionally, concentric measuring means 80 may be provided, with the inner shape sized to measure the dye and the outer shape sized to measure the developer.

After all of the materials have been dispensed from the dispensing containers in the metered amounts desired, a spatula or similar device can be used to blend the components so as to form an activated or developed dye capable of being applied to hair, for example, by a brush.

In accordance with the system described herein, additional containers including additional colors of dye may be provided. Containers including other components such as coupling agents, buffers and the like may also be provided and should be designed using the same criteria as described with relation to the hair dye and developer already discussed.

The present invention provides hair care professionals with a number of unique advantages not readily obtainable by the practices currently in use throughout the industry. As previously explained, the system eliminates the complexities of measuring and blending various hair dying formulations by providing such formulations in a limited number of preselected formats, e.g. pastes, creams or gels. Moreover, each of the formulations used are compatible with both the other possible ingredients and the other possible carrier formats used. The hair dying components, such as the dye and the developer, are also formulated such that they contain no intentionally undissolved material. The system of the present invention also provides activated hair dyes that will neither run nor be difficult to apply.

In addition, the present invention also provides a nearly "fool proof" method of measuring and dispensing correct amounts of one or more hair dyes and sufficient developer. This ensures a degree of repeatability and accuracy not otherwise obtainable from one batch of hair dye to the next.

The system of the present invention is also easily scaleable, which allows hair care professionals to prepare just enough hair dye to do a specific volume or area of hair, without having to produce a "full batch." The benefits of the easy scaleability of the system are also multiplied as the number of components increases, otherwise complicating dye formulation.

Furthermore, and in accordance with the present invention, a number of individual coloring compositions can be compounded quickly and easily without waste of time or material. Because the coloring and developer are provided in an easily proportionate ratio and in compatible delivery formats, the hair care professional will have both the time and the ability to create individual batches of coloring compounds of any volume desirable, without significant additional thought or effort.

Finally, the present invention provides the hair care professional with the ability to control the extent of the developing reaction between the hair dye and developer as needed. For example, an activatable oxidizable hair dye will completely react with a peroxide developer within about half of an hour in most cases. If a hair dying project is complicated and takes significant time, then there is a chance that the hair dye will be completely developed prior to its application. The hair care professional might then have to prepare a second "full" batch of hair dye formulation, not because additional material was needed, but rather because the material had essentially "gone bad."

In accordance with the present invention, however, a hair care professional has at least two choices. First, all of the materials necessary for a project can be measured out onto a blending board. However, rather than mixing the entire batch, only a few inches need be mixed at a time. When the first mixed portion is used up, then another small portion can be blended. Of course, eventually, the light in the shop will affect the peroxide in the developer. However, the developer should remain usable for the desired period of time.

Alternatively, the hair care professional can merely meter out small portions of dye and developer at a time. These portions would be blended and used. Thereafter, another small portion could be blended and used.

EXAMPLE 1

Hydrogen peroxide gel formulations in accordance with preferred aspects of the present invention were produced as follows.

| Hydrogen Peroxide Gel | | | |
|---|---|---|---|
| | % w/w | | |
| | 1 | 2 | 4 |
| Carbomer-Carbopol 940 (Goodrich) | 1.00 | 1.00 | 1.00 |
| Distilled water | 79.36 | 62.16 | 92.26 |
| Polyoxamer 407-Pluronic F-127 (BASF) | 2.00 | 2.00 | 2.00 |
| Hydrogen Peroxide (35%) | 17.20 | 34.40 | 4.30 |
| Triethanolamine | 0.44 | 0.44 | 0.44 |
| | 100.00 | 100.00 | 100.00 |
| | 20-Vol | 40-Vol | 5-Vol |

It will be understood that the examples and preferred embodiments set forth herein are representative and exemplary. They do not constitute the full range of the present invention nor do they encompass the equivalents thereof.

We claim:

1. A hair dying system, comprising:

an oxidative dye component having a preselected concentration of a developable oxidative hair dye;

a first dye reservoir containing said oxidative dye component;

a developer component having a preselected concentration of a developer capable of developing said oxidative hair dye;

a first developer reservoir containing said developer component;

dispensing means for dispensing said oxidative dye component from said first dye reservoir and for dispensing said developer component from said first developer reservoir, said dispensing means including a first orifice defining an outlet from said first dye reservoir, said first orifice having a cross-sectional area sized active to said concentration of oxidafire hair dye, and a second orifice defining an outlet from said first developer reservoir, said second orifice having a cross-sectional area sized relative to said concentration of said developer; and a blending means for blending together is dispensed quantity of said oxidative dye and developer components, wherein said blending means comprises a substantially fat-surface, inert material having a measuring means for measuring a dispensed quantity of at least one of said developer and said oxidative dye component disposed thereon, and wherein said blending means is detached from said first dye reservoir and said first developer reservoir.

2. The hair dying system as claimed in claim 1, wherein said blending means includes a plurality of leaves detachably connected together, whereby one of said plurality of leaves can be detached from a remainder of said plurality of leaves after use.

3. The hair dying system as claimed in claim 1, wherein said measuring means includes indicia arranged linearly on a substrate for measuring a dispensed length of at least one of said dye and developer components.

4. The hair dying system as claimed in claim 1, wherein said measuring means includes at least one geometric indicia sized and shaped to define a predetermined area, whereby covering said predetermined area with at least one of said dispensed dye and developer components determines said dispensed quantity of said at least one of said developer and dye components.

5. The hair dying system as claimed in claim 1, wherein said dye component has a viscosity such that said dye component does not spread substantially upon dispensing.

6. The hair dying system as claimed in claim 5, wherein said viscosity of said dye component is between about 500 cps. and about 3,000,000 cps.

7. The hair dying system as claimed in claim 6, wherein said viscosity of said dye component is between about 10,000 cps. and about 1,000,000 cps.

8. The hair dying system as claimed in claim 7, wherein said viscosity of said dye component is between about 20,000 cps. and about 500,000 cps.

9. The hair dying system as claimed in claim 1, wherein said dye component includes a carrier selected from the group consisting of gels, creams and pastes.

10. The hair dying system as claimed in claim 1, wherein said developer component has a viscosity such that said developer component does not spread substantially upon dispensing.

11. The hair dying system as claimed in claim 10, wherein said viscosity of said developer component is between about 20,000 cps. and about 3,000,000 cps.

12. The hair dying system as claimed in 11, wherein said viscosity of said developer component is between about 50,000 cps. and about 1,000,000 cps.

13. The hair dying system as claimed in claim 12, wherein said viscosity of said developer component is between about 70,000 cps. and about 500,000 cps.

14. The hair dying system as claimed in claim 1, wherein said developer component includes a carrier selected from the group consisting of gels, creams and pastes.

15. The hair dying system as claimed in claim 1, wherein said hair dye is an oxidative hair dye and said developer is a peroxide.

16. A method of formulating a hair dye composition, comprising the steps of:

providing an oxidative dye component having a preselected concentration of a developable oxidative hair dye, said oxidative dye component being contained in a first dye reservoir;

providing a developer component having a preselected concentration of a developer capable of developing said oxidative hair dye, said developer being contained in a first developer reservoir;

dispensing a quantity of said oxidative dye component from said first dye reservoir and a quantity of said developer component from said first developer reservoir with at least one means for dispensing said oxidative dye component from said first dye reservoir and for dispensing said developer component from said first developer reservoir, said dispensing means including a first orifice defining an outlet from said first dye reservoir, said first orifice having a cross-sectional area sized relative to said concentration of oxidative hair dye, and a second orifice defining an outlet from said first developer reservoir, said second orifice having a cross-sectional area sized relative to said concentration of said developer; wherein said quantities are dispensed onto a blending means for blending together a dispensed quantity of said oxidative dye and developer components, wherein said blending means comprises a substantially flat-surfaced, inert material which is detached from said first dye reservoir and said first developer reservoir;

measuring said dispensed quantities of said oxidative dye and developer components with a measuring means for measuring a dispensed quantity of at least one of said developer and said oxidative dye component, said measuring means being disposed on said blending means and wherein said blending means is detached from said first dye reservoir and said first developer reservoir; and intimately intermixing said dispensing quantities of said oxidative dye and developer components to develop said hair dye.

17. The method of claim 16 wherein said dispensed quantities of said oxidative hair dye and developer are dispensed as columns which are measured by comparison to said measuring means and wherein said measuring means is selected from the group consisting of indicia arranged linearly on said blending means and at least one geometric indicia sized and shaped to define a predetermined area.

* * * * *

UNITED STATES PATENT AND TRADEMARK OFFICE
CERTIFICATE OF CORRECTION

PATENT NO.  :  5,554,197

DATED  :  September 19, 1996

INVENTOR(S)  :  Assini et al.

It is certified that error appears in the above-identified patent and that said Letters Patent is hereby corrected as shown below:

Column 13, line 1, "active" should read --relative--.

Column 13, line 2, "oxidafire".should read --oxidative--.

Column 13, line 6, "is" should read --a--.

Column 13, line 9, "fat-surface" should read --flat-surfaced--.

Signed and Sealed this

Eleventh Day of February, 1997

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,554,197
DATED : September 10, 1996
INVENTOR(S) : Anthony Assini

It is certified that error appears in the above-identified patent and that said Letters Patent is hereby corrected as shown below:

On the cover page, delete inventor "Bernard Foss"

Signed and Sealed this

Twenty-second Day of April, 1997

Attest:

BRUCE LEHMAN

Attesting Officer

Commissioner of Patents and Trademarks